(12) United States Patent
Henderson et al.

(10) Patent No.: US 8,151,593 B2
(45) Date of Patent: Apr. 10, 2012

(54) EMBEDDING METHOD AND APPARATUS FOR THE PREPARATION OF FROZEN SECTION TISSUE

(75) Inventors: Colin Henderson, London (CA); Claire Temple-Oberle, London (CA)

(73) Assignee: London Health Sciences Centre Research Inc., London, Ontario (CA)

( * ) Notice: Subject to any disclaimer, the term of this patent is extended or adjusted under 35 U.S.C. 154(b) by 442 days.

(21) Appl. No.: 12/065,842

(22) PCT Filed: Sep. 7, 2006

(86) PCT No.: PCT/CA2006/001467
§ 371 (c)(1),
(2), (4) Date: Jul. 10, 2008

(87) PCT Pub. No.: WO2007/028243
PCT Pub. Date: Mar. 15, 2007

(65) Prior Publication Data
US 2009/0019865 A1    Jan. 22, 2009

Related U.S. Application Data

(60) Provisional application No. 60/714,894, filed on Sep. 8, 2005.

(51) Int. Cl.
*F25C 5/14* (2006.01)
(52) U.S. Cl. ............. 62/341; 62/62; 422/63; 436/174
(58) Field of Classification Search ................ 62/341, 62/62; 422/104, 63; 436/174
See application file for complete search history.

(56) References Cited

U.S. PATENT DOCUMENTS

| | | | |
|---|---|---|---|
| 3,982,862 A | 9/1976 | Pickett et al. | |
| 4,752,347 A | 6/1988 | Rada | |
| 5,550,033 A | 8/1996 | Krumdieck | |
| 5,644,919 A | 7/1997 | Baker et al. | |

(Continued)

FOREIGN PATENT DOCUMENTS

CA    2437425    8/2003
(Continued)

OTHER PUBLICATIONS

Abstract translation of DE3320349, Blutspendedienst Der Drk Lande Jun. 16, 2011.*

(Continued)

*Primary Examiner* — Cheryl J Tyler
*Assistant Examiner* — Jonathan Koagel
(74) *Attorney, Agent, or Firm* — Bereskin & Parr LLP

(57) ABSTRACT

Various embodiments for an apparatus and method for preparing frozen tissue specimens are described. In an exemplary embodiment, the apparatus includes a sample container for receiving an excised tissue sample and embedding material. The sample container includes a flat base along which the tissue sample is flattened. The apparatus further includes a freezing box with a freezing platform and a freezing agent. The sample container is placed on the freezing platform to begin the freezing process. A chuck with a generally planar surface can be placed on the sample container during the freezing process joining the chuck, tissue specimen, and sample container base in generally parallel planes. In some cases, the sample container can be made from a suitable material, such as plastic, that is at least semi-transparent to allow visual confirmation of tissue flatness and freezing.

23 Claims, 7 Drawing Sheets

U.S. PATENT DOCUMENTS

| | | | | |
|---|---|---|---|---|
| 5,983,991 | A | 11/1999 | Franks | |
| 6,209,343 | B1 * | 4/2001 | Owen | 62/457.2 |
| 6,467,299 | B1 * | 10/2002 | Coetzee | 62/457.2 |
| 6,536,219 | B2 | 3/2003 | Peters | |
| 6,558,629 | B1 | 5/2003 | Davidson | |
| 7,234,308 | B1 * | 6/2007 | Critz | 62/51.1 |

FOREIGN PATENT DOCUMENTS

| | | |
|---|---|---|
| DE | 3320349 A1 * | 12/1984 |

OTHER PUBLICATIONS

International Searching Authority (Canada), International Search Report, PCT Applicaiton No. PCT/CA2006/001467, Mar. 20, 2008.
Shriner, DL; McCoy, DK; Goldberg, DJ; Wagner, RF Jr., Mohs Micrographic Surgery. J Am Acad Dermatol, Jul. 1998 39(1):79-97.
Snow, SN; Madjar DD Jr; Mohs Surgery in the Management of Cutaneous malignancies. Clin Dermatol May-Jun. 2001 19(3):339-47.
Cottel, WI;Proper, S Mohs surgery, fresh tissue technique. Our Technique with a review. J. Dermatol Surg Oncol. Jul. 1982 8(7):576-87.
Mons, FE; Guyer, MF. Pre-exicisonal fixation of tissues in the treatment of cancer in rats. Cancer Res. 1941 1:49-51.
Mohs,FE. Chemosurgery: A microscpically controlled method of cancer excision. Arch Surg. 1941 42:279-295.
Leshin, B; Cook,SR; Frye, DW. Cryomold: a device for tissue embedding in Mohs micrographic surgery. J. Dermatol Surg Oncol. Mar. 1991 17(3):234-6.
Tramovitch, TA; Stegeman SJ. Microscopically controlled excision of skin tumors. Arch Dermatol. Aug. 1974 110(2):231-2.
Honda, N; Friedrnan, D. A simple method of tissue embedding for Mohs micrgraphic surgery. J Dermatol Surg Oncol. May 1989 15(5):502-4.
Hanke, CW; Menn, H; O'Brian, JJ. Chemosurgical reports: frozen-section processing with the Miami special. J Dermatol Surg Oncol. Apr. 1983 9(4):260-2.
Nouri, K; Olconnell, C; Alonso, J; Rivas, MP, Alonso, Y. The Miami special: a simple tool for quality section mounting in Mohs surgery. J Drugs Dermatol. Mar.-Apr. 2004 3(2):175-7.
Dogan, MN;Snow, SN; Lo, J. Rapid skin edge elevation using the OCT compound droplet technique to obtain horizontal microsections in Mohs Micrographic surgery. J Dermatol Surg Oncol. Nov. 17, 1991 (7):857-60.
Carter, VH. A new method for preparing tissue blocks for cryostat sectioning. J Dermatol Surg Oncol. Jul. 11, 1985 (7):687-9.
Miller, LJ; Argenyl, ZB; Whitaker, DC. The preparation of frozen sections for micrographic surgery. A review of current methodology. J Dermatol Surg Oncol. Nov. 1993 19(11):1023.
Hanke, CW; Lee, MW. Cryostat use and tissue processing in Mohs micrographic surgery. J Dermatol Surg Oncol. Jan. 1989 15(1):29-32.
Silapunt, S; Peterson, SR; Alcalay, J; Goldberg, LH. Mohs tissue mapping and processing: a survey study. Dermatol 1 Surg. Nov. 2003 29(11):11 09-12.
International Searching Authority (Canada), International Search Report, PCT Application PCT/CA2006/001467, dated Dec. 28, 2006.
Peters, Sr. The art of embedding tissue for frozen section. Part 1: A system for precision face down cryoembedding of tissue using freezing temperature embedding wells. J.Histotechnol 26:11-19.
Bielinski K: Cryomold use in Moh;s micrographic surgery. Dermatol Nurs 17:370-372, 2005.
Cryo Caddy Video, Oct. 13, 2011, [online], [retrieved Oct. 24, 2011], Retrieved from You Tube using Internet: <URL: http://www.youtube.com/watch?v=z1irRdSd9VA>.

* cited by examiner

EMBEDDING METHOD AND APPARATUS FOR THE PREPARATION OF FROZEN SECTION TISSUE

FIELD

Various aspects of the embodiments described herein relate to the field of tissue sample preparation. More particularly, the embodiments described herein relate to a method and apparatus for the preparation of frozen section tissue samples.

BACKGROUND

In one well-known frozen section procedure, a cold chuck is retrieved from a cryostat (at approximately −20 degrees Celsius). A small amount of a viscous embedding material, which is also known as a tissue freezing compound, is placed on the generally planar surface of the chuck, which may be textured, and the tissue sample is then placed into the embedding material. The embedding material may be OCT (Optimum Cutting Temperature); e.g. Tissue-Tek™ provided by Sakura Finetek. The combination of OCT and the tissue sample is referred to herein as a tissue specimen. It is generally understood that the tissue specimen is supported on a platform (such as a chuck) and/or contained in a receptacle (such as a mold). The chuck and tissue specimen are then placed back into the cryostat chamber and cooled until the tissue specimen is frozen. During this freezing process, a heat sink, also known as a weighted heat extractor, may be placed onto the tissue specimen to flatten the tissue sample and accelerate the freezing process. The frozen tissue sample is then sectioned using a microtome/cryostat. A section is typically several micrometers thick. The sections are then processed by methods that are well known to those skilled in the art. A medical practitioner then evaluates the processed sections.

The ability to produce full face microscopic sections of the true deep margin of the excised tissue relies on three important steps in the frozen section process. First of all, the tissue must be laid down so that the deep margin of the tissue lies in the same plane. Secondly, this planar orientation must be maintained during freezing. Finally, the frozen tissue sample needs to be oriented parallel to the sectioning plane of the microtome. A breach of any of these steps can result in excessive microtome "trimming in" before a full face section is obtained, potentially exposing a portion of a tumor which did not extend to the true deep margin.

SUMMARY

In one aspect, at least one embodiment described herein provides an apparatus for preparing a frozen tissue specimen from an excised tissue sample. The apparatus comprises a freezing box including a first base, a lid that covers the first base, and a freezing chamber defined by the first base and the lid, the freezing chamber being adapted for receiving a freezing agent and the freezing box being made from a thermal insulating material for maintaining a reduced temperature environment in the freezing chamber for freezing the excised tissue sample. The apparatus further comprises a freezing platform having a flat freezing surface. The apparatus also comprises at least one sample container configured for receiving, in use, the excised tissue sample and the embedding material, the at least one sample container including a well having a flat second base, walls and flat flanges connected at the upper portion of the walls to define a flat surface; and at least one chuck, the at least one chuck having a generally planar surface for placement on the flat flanges of the sample container.

The sample container can be made from plastic material that is at least semi-transparent to enable visual confirmation of the flattening of the excised tissue sample and the freezing of the excised tissue sample and the embedding material.

At least one of the flanges of the at least one sample container can be longer than the other flanges of the at least one sample container.

At least one of the walls of the well of the at least one sample container can be beveled.

The freezing agent can comprise dry ice and the reduced temperature environment is at less than −70 degrees Celsius.

The freezing platform and the freezing chamber can be sized to provide gaps between the freezing chamber and the freezing platform for receiving at least one of: one or more pieces of dry ice and additional insulating material.

The freezing agent can comprise one of compressed carbon dioxide gas, compressed liquid nitrogen, and a mechanical refrigeration compressor.

The thermal insulating material can comprise polystyrene.

The freezing platform can comprise anodized aluminum.

The freezing platform can comprise one of copper, stainless steel, aluminum and alloys thereof.

The flat freezing surface can comprise at least one of a bare metal, anodized, glazed, painted, and ceramic surface.

The at least one chuck can comprise a post mounted opposite the generally planar surface and the freezing platform comprises at least one hole sized to receive the post.

The holes in the freezing platform can extend from the top of the freezing platform to the bottom of the freezing platform.

The first base of the freezing box can comprise shoulders for receiving and providing support for the freezing platform, the shoulders having a height for placing the upper surface of the freezing platform approximately level with the upper surface of the first base.

The first base of the freezing box can comprise a first securing member and the lid comprises a complementary second securing member sized for releasably engaging the first securing member when the lid is placed on the first base.

In another aspect, at least one embodiment described herein provides a method for preparing a frozen tissue specimen from an excised tissue sample. The method comprises:

a) placing the excised tissue sample into a sample container having a well with a lower flat base, and upper flat flanges;

b) flattening the excised tissue sample along the flat base of the well of the sample container;

c) adding a sufficient amount of embedding material to the well of the sample container after the excised tissue sample has been flattened, wherein a top portion of the embedding material is above the flanges of the sample container;

d) placing the flat base of the sample container on a flat freezing surface of a freezing platform, the freezing platform being maintained at a reduced temperature for freezing the excised tissue sample and the embedding material; and e) placing a chuck on the sample container for a first time period, the chuck having a generally planar surface that is placed on the flat flanges of the sample container to maintain a flat contact surface therewith.

The method may further comprise:
  f) inverting the chuck and placing the inverted chuck, tissue specimen and sample container on the freezing platform for a second time period; and
  g) removing the sample container from the chuck and tissue specimen after the excised tissue sample and the embedding material has frozen.

The chuck can comprise a post and the freezing platform can comprise a hole sized to receive the post, and the inverting step can further comprise placing the post into the hole.

The method can further comprise maintaining the sample container and the chuck in the range of 10 to 25 degrees Celsius prior to freezing.

The method can comprise placing the freezing platform in a freezing chamber of a freezing box, and using a freezing agent in the freezing chamber for maintaining the freezing platform at a reduced temperature.

The method can further comprise using dry ice as the freezing agent to maintain the reduced temperature environment at less than −70 degrees Celsius.

The method can further comprise using one of compressed carbon dioxide gas, compressed liquid nitrogen, and a mechanical refrigeration compressor as the freezing agent.

The sample container can be at least semi-transparent and the method can further comprise visually confirming the flattening of the excised tissue sample and the freezing of the excised tissue sample and the embedding material.

In another aspect, at least one embodiment described herein provides a sample container for use in preparing a frozen tissue specimen from an excised tissue sample. The sample container comprises a flat base and walls extending upwardly from the flat base thereby defining a well for receiving, in use, the excised tissue sample and an embedding material; and, flat flanges connected at upper portions of the walls to define an upper flat surface for the sample container and accommodate any overflow of the embedding material.

The sample container can be made from material that is at least semi-transparent to enable visual confirmation of flattening of the excised tissue sample and freezing of the tissue sample and the embedding material.

The material for the sample container can be a plastic that is suitable for withstanding temperatures in the range of about room temperature to −80 degrees Celsius.

At least one of the flanges of the sample container can be longer than the other flanges.

At least one of the walls of the sample container can be beveled.

BRIEF DESCRIPTION OF THE DRAWINGS

For a better understanding of various embodiments described herein and to show more clearly how they may be carried into effect, reference will now be made, by way of example only, to the accompanying drawings which show at least one exemplary embodiment and in which.

DETAILED DESCRIPTION

Figure 1:
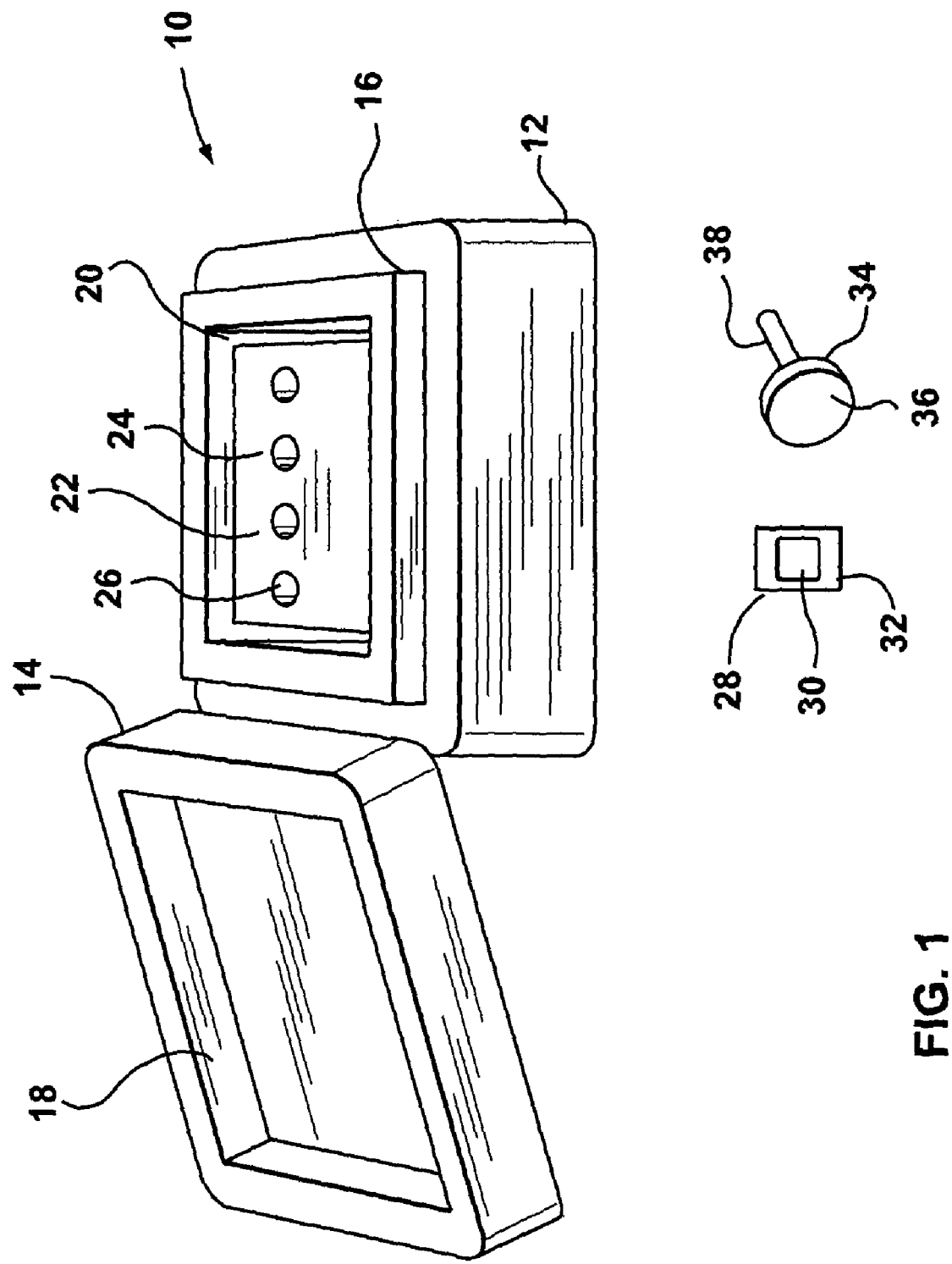
FIG. 1 is a diagram of an exemplary embodiment of a freezing apparatus that can be used to prepare frozen tissue specimens.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the various embodiments described herein. Some features in the figures have not been drawn to scale. Further, it should be understood by those of ordinary skill in the art that the embodiments described herein may be practiced without these specific details. In other instances, well-known methods, procedures and components have not been described in detail so as not to obscure the embodiments described herein. Furthermore, this description should not be considered as limiting the scope of the embodiments described herein, but rather as merely describing the implementation of the various embodiments described herein.

An apparatus and method for preparing a frozen tissue specimen that can be sectioned using a suitable cutting device, such as the microtome in a cryostat, is described herein. A portion of the method involves inserting a tissue sample into a sample container, also known as a platform mold, adding an embedding medium and then joining a chuck to the sample container and cooling the contents of the sample container to produce the frozen tissue specimen. It should be understood that the embedding medium is analogous to a tissue freezing compound. The cooling step can be performed using a cooling box that has a cooling chamber and a freezing platform. The cooling box is kept outside of the cryostat chamber. In some embodiments, the cooling chamber may include dry ice to cool the freezing chamber, which allows the cooling box to be self-contained, portable and have small dimensions. The frozen tissue specimen preparation method is rapid, simple to perform and highly reliable for processing various tissue samples including multiple small tissue fragments, needle biopsies, irregular surfaces and Mohs samples.

Referring now to FIG. 1, shown therein is a diagram of an exemplary embodiment of a freezing apparatus that can be used to prepare frozen tissue specimens. The freezing apparatus includes a freezing box 10 having a base 12 and a lid 14. The base 12 includes a first securing member 16 that is sized for releasably engaging a complementary second securing member 18 that is located on the underside of the lid 14. The freezing box 10 further includes a freezing chamber 20. A freezing agent (not shown) is placed within the freezing chamber 20 to maintain the freezing chamber 20 at a temperature that is suitable for preparing frozen tissue specimens. The base 12 and the lid 14 are made from a suitable insulating material to maintain the interior of the freezing box 10 at a suitable cold temperature, which is described in more detail below.

The freezing apparatus further includes a freezing platform 22 that is placed within the freezing chamber 20. Once the freezing platform 22 has been cooled, it acts as a heat sink to cool any object that is placed in contact with it. The freezing platform 22 includes a flat freezing surface 24, and several holes 26 (only one of which is labeled for simplicity). In some embodiments, the freezing platform 22 is smaller than the freezing chamber 20 so that there are gaps when the freezing platform 22 is placed within the freezing chamber 20. In some embodiments, the freezing platform 22 is sized so that the gaps are large enough to accommodate the freezing agent or additional insulating material. The freezing platform 20 can also be sized so that some edges of the freezing platform 22 contact corresponding sides of the freezing chamber 20. This anchors the freezing platform 22 and also ensures that the insulating walls of the freezing chamber 20 are in close contact with at least some sides of the freezing platform 22 so that the freezing platform 22 is maintained at a cold temperature.

The freezing apparatus further includes a sample container 28 for holding a tissue sample and embedding material. It should be understood that the sample container 28 can also be considered to be a platform mold. The sample container 28 includes a well 30 with a flat base for receiving the tissue sample and the embedding material, and flanges 32. The flat bottom of the well 30 acts as a conforming plane for tissue flattening. The flanges 32 accommodate any overflow of the embedding material. A sufficient amount of the embedding material is added to the well 30 so that a portion of the embedding material lies above the plane defined by the flanges 32; this portion of the embedding material engages chuck grooves (described below) for forming a better bond during freezing. The flanges 32 also provide ease of handling during the preparation of the frozen tissue specimen. The flanges 32 also ensure that the conforming plane and a chuck surface are parallel to each other. The flanges 32 do not have to be of equal size.

The freezing apparatus further includes a chuck 34 having a disc with a generally planar surface 36 and a post 38 mounted opposite the textured surface 36. The chuck 34 does not have to have a disc shape and can generally have any shaped planar configuration (i.e. disc, square, rectangle, elliptical, and the like) at its working end (i.e. the portion of the chuck 34 that makes contact with the embedding material and the sample container). Furthermore, it may be possible to use a chuck that does not have a post. The generally planar surface 36 includes a pattern of small grooves or cross-hatches that provide a "gripping surface" for the embedding material when it freezes thereby facilitating a bond between the embedding medium in the sample container 28 and the chuck 34. The textured surface of the chuck 34 can be considered to be generally oriented in a plane; hence surface 36 is referred to as being generally planar. The chuck 34 is used with the sample container 28 for preparing the frozen tissue specimen. The generally planar surface 36 of the chuck 34, when parallel to the flanges 32, ensures that the sample tissue and the surface 36 are generally parallel to each other. This is accomplished by placing the chuck 34 on top of the sample container 28, after the sample tissue and embedding material have been added to the sample container 28, so that the flanges 32 lie flat against the generally planar surface 36 of the chuck 34. Further, the holes 26 on the freezing platform 22 are sized slightly larger than the post 38 of the chuck 34 so that the chuck 34 can be inverted and inserted at the top of the freezing platform 22 to increase the contact area between the chuck 34 and the freezing platform to further accelerate the freezing process.

Although only one sample container 28 and one chuck 34 are shown in FIG. 1, it should be understood that there can be several sets of sample containers 28 and chucks 34 so that more than one frozen tissue specimen can be prepared at the same time. For example, with the freezing platform 22, up to four frozen tissue specimens may be prepared at the same time. However, there may be other embodiments with a larger or smaller number of holes 26 in the freezing platform 24 and hence more or fewer frozen tissue specimens can be prepared simultaneously. Accordingly, the size of the freezing platform 22 and the freezing box 10 can be changed to accommodate the preparation of a greater or fewer number of frozen tissue specimens.

Figure 2A:
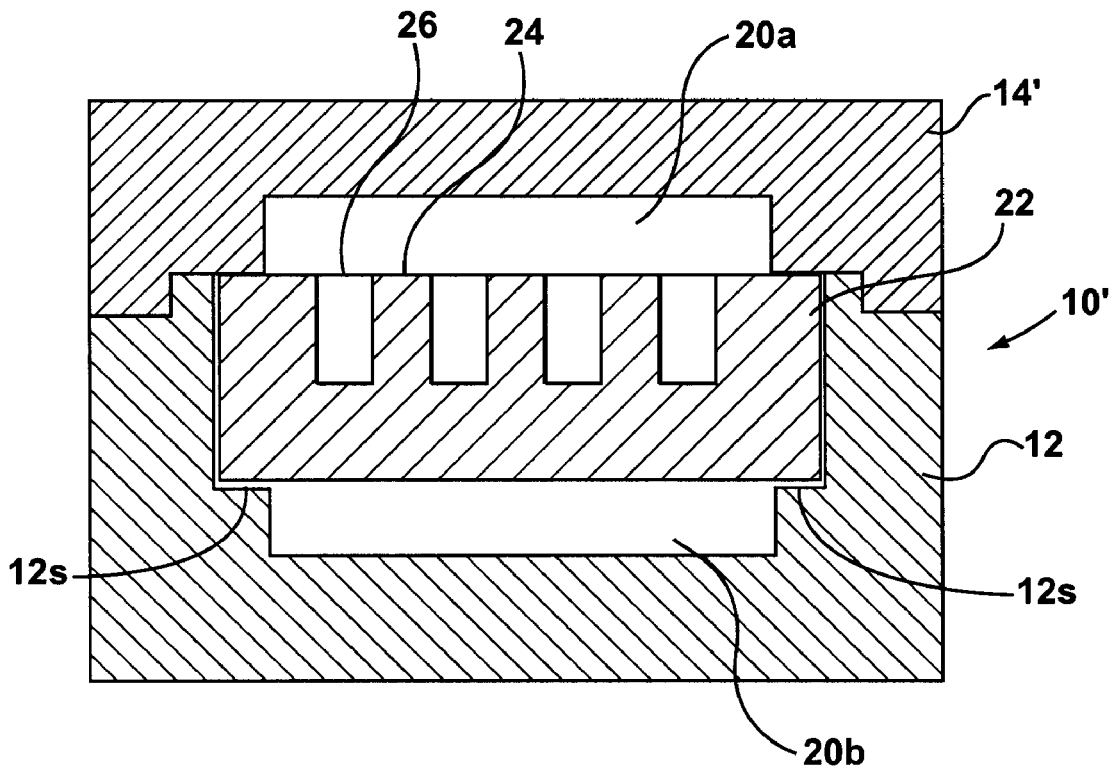
FIG. 2A is a cross-sectional side view of a freezing box and a freezing platform that can be used as part of the freezing apparatus.
Figure 2B:
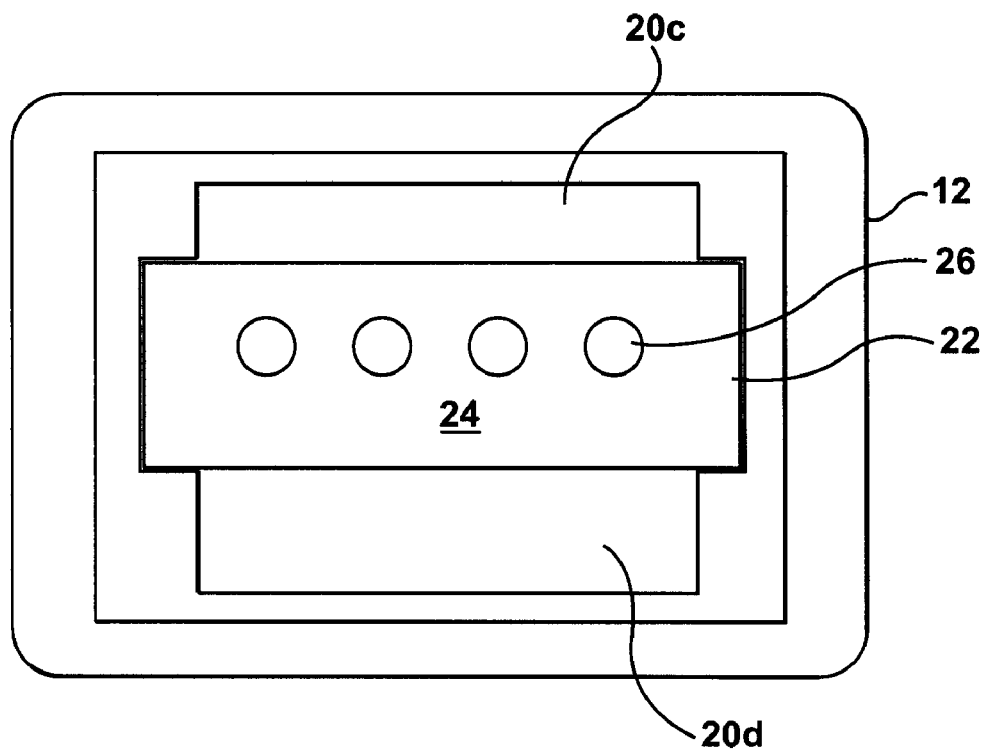
FIG. 2B is a top view of the freezing box and freezing platform of FIG. 2A.

Referring now to FIGS. 2A and 2B, shown therein are a cross-sectional side view and a top view, respectively, of the freezing platform 22 and an alternative embodiment of the freezing box 10'. The base 12 of the freezing box 10' includes shoulders 12s to support the freezing platform 22 and provide a gap 20b underneath the freezing platform 22. The height of the shoulders 12s can be selected so that the top surface of the freezing platform 22 is approximately level with the top of the base 12 when the lid 14' is off. This makes it easier to work with the freezing platform 22 while preparing the frozen tissue specimen. The width of the shoulders 12s is chosen to provide enough support for the freezing platform 22. In some embodiments with larger freezing platforms, there may be additional support in the base 12 of the freezing box 10'. The additional support may be located centrally.

In one implementation, the base 12' and lid 14 may be made from polystyrene, such as Styrofoam™. In other implementations, a hard shell insulated material may be used rather than polystyrene. In other embodiments, other materials that can provide suitable insulation can also be used.

Once the freezing platform 22 is placed within the freezing box 12' and the lid 14' is placed on the base 12', there are gaps 20a, 20b, 20c and 20d that can be sized to accommodate the freezing agent. In some embodiments, the freezing agent can be dry ice. In this case, the freezing platform 22 and the freezing box 12' can be sized so that the gaps 20a, 20b, 20c and 20d can accommodate one or more slabs of dry ice, which may be in the order of 4 cm thick. Ideally, the gaps are sized just slightly larger than the slabs of dry ice to allow the slabs of dry ice to be slid into and out of position as needed and to more efficiently conduct heat away from the freezing platform 22. In some embodiments, the gaps 20c and 20d may be about 3 cm wide. Prior to placing the freezing platform 22 into the freezing chamber 20, an appropriate number of slabs of dry ice are placed in the gap 20b. In other instances, the slabs of dry ice can be broken into smaller chunks, which are then placed within one or more of the gaps 20a-20d. Alternatively, chips of dry ice can also be used. In either case, the size of the gaps can be reduced. The freezing platform 22 is then placed within the freezing chamber 20. Other pieces of dry ice can then be placed in the gaps 20c and 20d. The gap 20a provides space for pieces of dry ice and/or sample containers and inverted chucks (an inverted chuck has its post engaging one of the holes 26). For instance, pieces of dry ice may be placed in the gap 20a when the freezing platform 22 is being cooled in preparation for freezing a tissue sample. Once the freezing platform 22 has been cooled, then the pieces of dry ice in the gap 20a can be removed and the sample container 28 can be placed on the freezing platform 22. In one implementation, the gap 20a can have a height of about 3 cm.

When dry ice is used as the freezing agent, the interior of the freezing box 10 is maintained at a temperature of about −78 degrees Celsius. This is in contrast to the interior of the cryostat, which is typically used for freezing the tissue specimen in many conventionally used methods. The interior of the cryostat is maintained at about −22 degrees Celsius. The lower temperature of the freezing box 10 accelerates the freezing process and allows frozen tissue specimens to be prepared much faster than if the cryostat or some other device was used that does not operate at such a low temperature. The amount of dry ice that is required depends on several variables including the degree of insulation provided by the freezing box 10, the amount of time that the freezing box 10 remains open (i.e. the lid 14 is removed), the amount of time spent pre-cooling the freezing plate 22, etc. In some embodiments, 2 kg of dry ice is sufficient for an entire day of operation of the freezing box 10.

Freezing is complete when the OCT reaches a core temperature of about −18 degrees Celsius, at which point the chuck and frozen tissue specimen can be transferred to the cryostat for sectioning. If the chuck and frozen tissue specimen are too cold, then they can be warmed up in the cryostat to the proper temperature required for sectioning. Using a lower temperature in the freezing box 10 virtually eliminates the visible ice crystal artifact. However, the sample container 28 needs to be made of a suitable material that can withstand the low temperature.

Cooling with dry ice, rather than other freezing agents, can be done for safety reasons, the low temperature provided by dry ice and the easy availability of dry ice. Housing the freezing platform 22 and dry ice in a fitted insulating container renders the freezing box 10 completely transportable, obviating the need for a bulky compressor or electrical connection. Frozen tissue specimen preparation with the freezing box 10 is as fast as or faster than traditional preparation techniques. The freezing box 10 has sufficient thermal inertia to allow the preparation of multiple blocks over several hours, which can allow the cryostat to be dedicated to cutting frozen tissue specimens.

However, in alternative embodiments, the freezing agent may be provided by an alternate means. For example, compressed carbon dioxide gas, compressed liquid nitrogen, a mechanical refrigeration compressor, or other suitable means may be used to cool the interior of the cooling box 10. The mechanical refrigeration compressor may or may not include a thermoelectric device (such as a Peltier device). In another embodiment, the freezing platform 22 can be cooled in a low temperature refrigeration unit and then transferred to the freezing box 10 for short-term use. For instance, the freezing platform 22 can be stored in a freezer that is at about −70 degrees Celsius, and then taken from there to the operating room for use. In this instance, the space (i.e. gaps) designed to hold dry ice can be occupied by one or more insulating inserts.

In general, if a cooling strategy other than dry ice is used, then design changes can be made to the freezing platform 22 and/or the cooling box 10, such as a change in box dimensions, to accommodate the different cooling strategy. Further, if a cooling strategy other than dry ice is used, then changes can be made to the sample container 28 such as the type of material that is used. This may have to be done due to the different temperatures that will be encountered in the freezing box 10 due to the use of a different freezing agent. For instance, if liquid nitrogen is used as the freezing agent, the temperature within the freezing box 10 will be about −195 degrees Celsius.

Figure 3A:
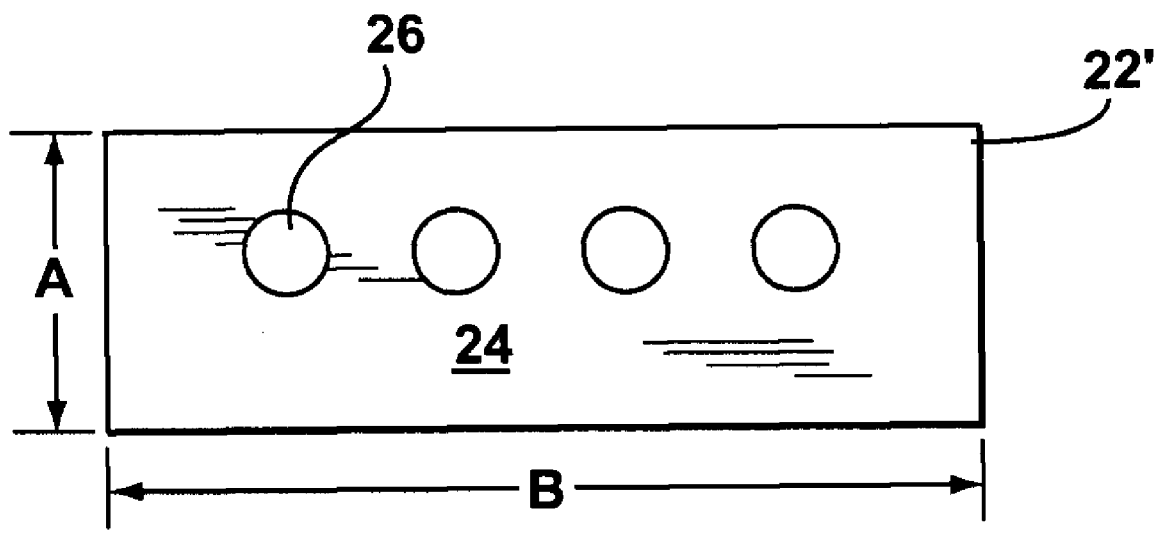
FIG. 3A is a top view of a freezing platform.
Figure 3B:
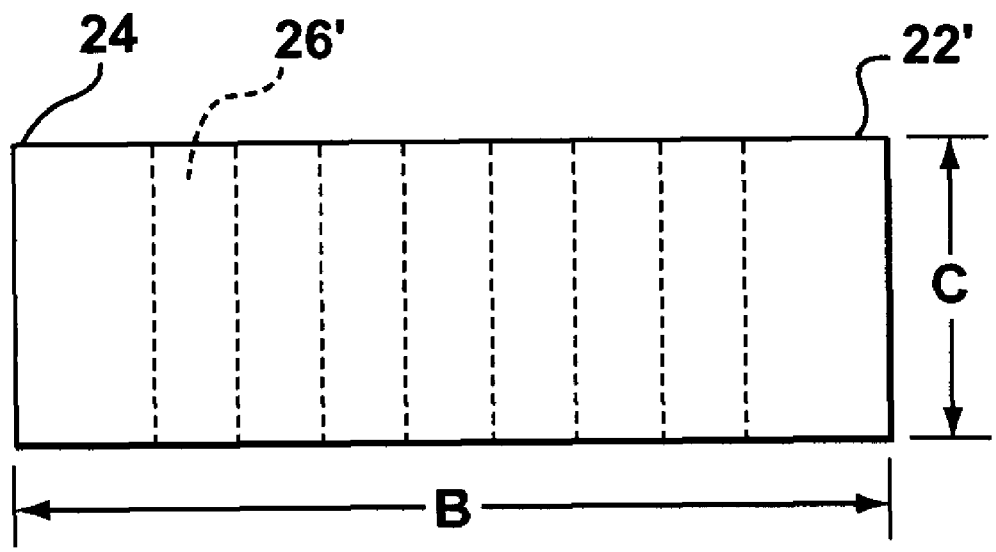
FIG. 3B is a side view of the freezing platform of FIG. 3A.

Referring now to FIGS. 3A and 3B, shown therein are top and side views of a different embodiment of the freezing platform 22'. The holes 26' travel from the top to the bottom of the freezing platform 22'. This allows any debris to fall out of the bottom of the freezing platform 22' rather than plugging any of the holes 26'. This also allows the holes 26' to accommodate various lengths of the chuck post 38 as well as allowing any debris to fall through. Holes made in this fashion also allow either side of the freezing platform 22' to be used as the cooling platform (i.e. work surface).

The freezing platform 22' may be made from anodized aluminum. Aluminum has low cost, is light-weight and has good thermal conductive properties. The highly polished and anodized surfaces of the freezing platform 22' facilitate optimum contact with the sample container 28 and/or chuck 34 and therefore maximum heat transfer. The anodized surfaces are also durable. In other implementations, the freezing platform 22' may be made from a different metal such as copper, stainless steel, an aluminum alloy and alloys thereof. For example, alloys of stainless steel may include chromium, nickel, manganese, molybedium and titanium. Furthermore, the surface of the freezing platform may generally be anodized, glazed, ceramic or painted. Using a different metal may require design changes in the dimensions of the freezing platform 22' due to the different weight of the different materials. Various exemplary dimensions for different designs of the freezing platform 22 are shown in Table 1. For at least some of these designs, the holes 26 can be located about 2 cm from the rear edge of the freezing platform 22' and 2 cm, 6 cm, 10 cm, and 14 cm from the left edge of the freezing platform 22'.

TABLE 1

Exemplary sizes for the Freezing Platform

| Design | Number of Holes | Hole diameter (mm) | Length B (cm) | Height C (cm) | Width A (cm) |
|---|---|---|---|---|---|
| 1 | 2 | 10 | 8 | 5 | 6 |
| 2 | 4 | 10 | 16 | 6 | 10 |
| 3 | 6 | 10 | 25 | 6 | 10 |
| 4 | 8 | 10 | 32 | 6 | 10 |
| 5 | 4 | 10 | 16 | 8 | 5 |
| 6 | 2 | 10 | 16 | 8 | 4 |
| 7 | 6 | 10 | 24 | 10 | 8 |
| 8 | 8 | 10 | 32 | 12 | 10 |

Figure 4A:
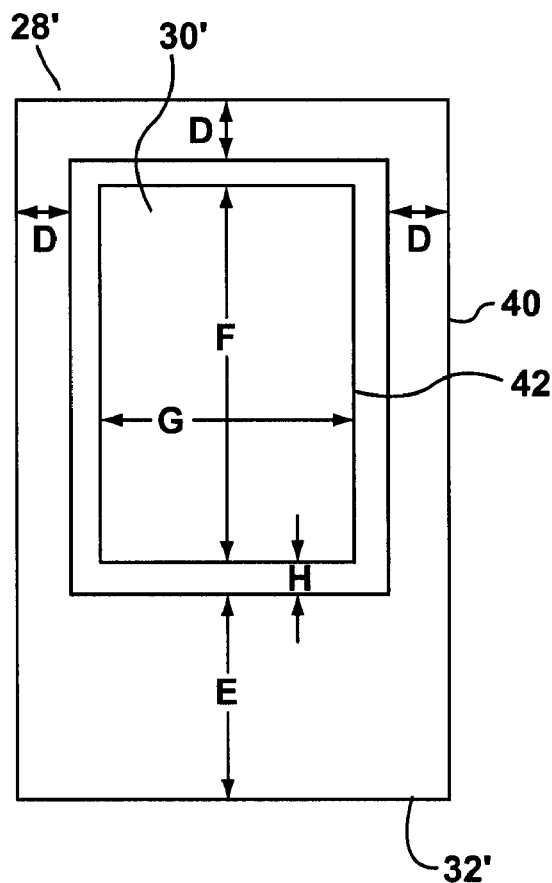
FIG. 4A is a top view of an exemplary embodiment of a sample container of the freezing apparatus of FIG. 1.
Figure 4B:
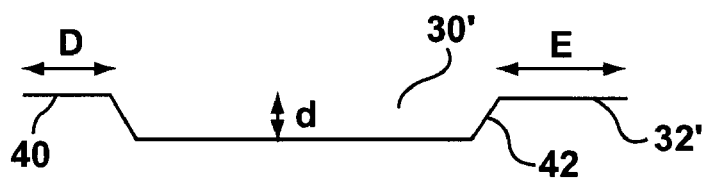
FIG. 4B is a cross-sectional side view of the sample container of FIG. 4A.
Figure 4C:
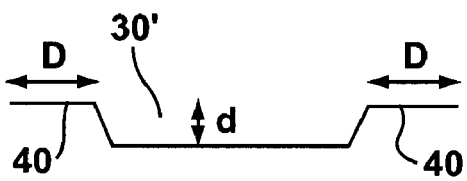
FIG. 4C is a cross-sectional front view of the sample container of FIG. 4A.
Figure 6A:
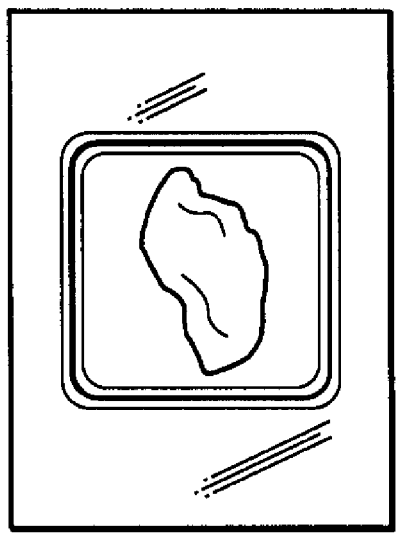
Figure 6B:
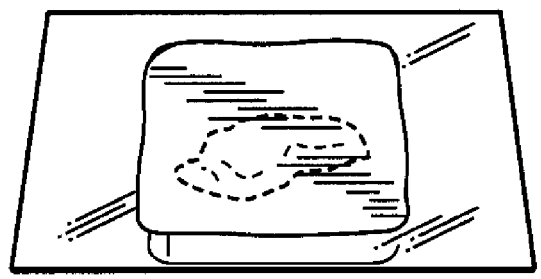

Referring now to FIGS. 4A-4C, shown therein respectively is a top view, a cross-sectional side view, and a cross-sectional front view of an exemplary embodiment of a sample container 28' that can be used in the freezing apparatus. In this exemplary implementation, the sample container 28' can include a longer bottom flange (or tab) 32' in comparison with the side and top flanges 40 (only one of which has been labeled for simplicity). This makes it easier to separate the sample container 28' from the chuck and tissue specimen once freezing is complete. This larger tab may also serve as both a writing surface (for tissue sample identification) and a pull-tab for separating the sample container 28' from the chuck and tissue specimen. In other embodiments, more than one side of the sample container may have a larger tab (see FIG. 6A for example).

As shown, the flanges 40, 32' have flat surfaces so that a flat contact is made with the generally planar surface 36 of the chuck 34. The sample container 28' also has a well 30' that may have beveled edges 42. In other implementations, only one wall of the well 30' may have a beveled edge. Beveled edges make it easier to separate the chuck and frozen tissue specimen from the sample container 28'. The beveled edges also provide lateral clearance for scalpel and forceps while flattening/relaxing the excised tissue onto the conforming plane of the base of the sample container 28. The well 30 can be square, rectangular, oval, or round. Straight edges can also be used for the walls of the well 30'.

The sample container 28' can be made having a variety of different sizes for the dimensions D, E, F, G and H. Exemplary sizes are shown in Table 2. Different depths can also be used for different size sample containers.

TABLE 2

Exemplary sizes for the Sample container

| Design | D (mm) | E (mm) | F (mm) | G (mm) | H (mm) | d (mm) |
|---|---|---|---|---|---|---|
| 1 | 5 | 15 | 15 | 15 | 1 | 4 |
| 2 | 5 | 15 | 25 | 20 | 1 | 5 |
| 3 | 5 | 15 | 28 | 24 | 2 | 6 |
| 4 | 5 | 20 | 15 | 15 | 1 | 5 |
| 5 | 5 | 15 | 24 | 24 | 2 | 5 |
| 6 | 5 | 15 | 34 | 24 | 2 | 5 |

In some embodiments, the sample container 28' can be made from a plastic material that remains pliable enough at the low temperatures encountered in the freezing box 10 so that the sample container 28' can be peeled from the chuck and frozen tissue specimen. Some plastics can only be used for temperatures as low as −20 degrees Celsius and these plastics become very brittle at −78 degrees Celsius and are not suitable for use in the freezing box 10. The plastic material that is used for the sample container 28' is also rigid enough at or near room temperature to maintain its shape under moderate compression (i.e. when receiving the chuck 34), yet remains flexible enough at very low temperatures (−78 degrees Celsius) so that it does not split or crack when flexed (to facilitate separation from the chuck and tissue specimen after freezing). Furthermore, when rapidly cooled, the plastic material that is used for the sample container 28' will not distort or buckle but maintain its shape. An example of one such plastic material that may be used is the plastic material that is similar to that used in the Tissue Prep Disposable Base Molds made by Fisher Scientific.

The plastic that is used for the sample container 30' can be transparent or at least semi-transparent to facilitate viewing of the tissue sample from below for "flatness". This enables visual confirmation of tissue flattening by inspecting the tissue sample through the transparent bottom of the sample container 28', so that the tissue orientation can be manipulated, if need be, before freezing commences. At this point, the tissue sample can be easily re-positioned since freezing has not yet been applied to the tissue sample and the embedding material. For example, the transparent nature of the sample container 28' allows for the deep margins to be pressed into the conforming plane on the bottom of the well 30 of the sample container 28 and visual confirmation that the tissue margin is completely flat.

Figure 5:
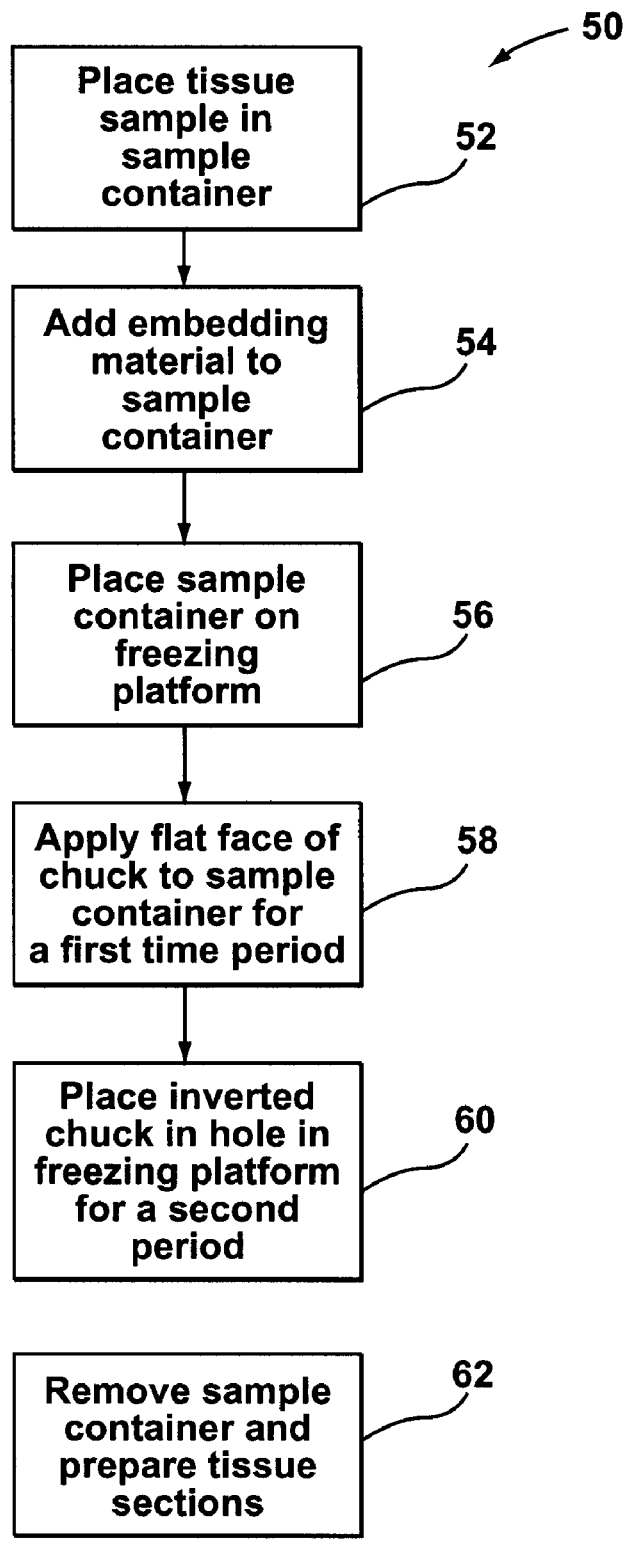
FIG. 5 is an exemplary embodiment of a flowchart of a frozen tissue specimen preparation method; and, FIGS. 6A-6D are illustrations of various steps of the frozen tissue specimen preparation method.

Referring now to FIG. 5, shown therein is an exemplary embodiment of a flowchart for a frozen tissue specimen preparation method 50. The method 50 begins at step 52 in which the excised tissue sample is placed on the dry surface of the bottom of the sample container 28. The deep margin of the tissue sample is oriented along a single plane at the bottom of the sample container 28 (see FIG. 6A), which maintains tissue "flatness". The tissue sample is then allowed to "relax" so that it is lying flat; this may require further manipulation and can be confirmed visually. Once the tissue sample is oriented, it will stick to the bottom of the sample container 28 through a combination of capillary action and protein adhesion. This adhesion occurs to the extent that the sample container 28 can be inverted without dislodging the tissue sample. The ability to orient tissue samples and have them stay stationary allows for the possibility of orienting sample tissue within an operating room or clinic, and then transporting the sample container 28 and tissue sample to a frozen section room for cutting. Due to the direct contact of the tissue sample and the sample container 28, the embedding medium does not obscure the view of the tissue sample after freezing, which allows for a minimization of "trimming in". The temperature of the sample container 28 can be in the range of 10 to 25 degrees Celsius so that the tissue sample can be manipulated so that it is flat. The tissue sample will become rigid for lower temperatures which can affect its ability to be flattened.

In step 54, a sufficient amount of the embedding material is added to the sample container 28 such that the sample container 28 is slightly overfilled; this ensures that the generally planar surface 36 contacts the embedding material during freezing. This allows some of the embedding material, via capillary action, to flow up into the grooves that are located on the generally planar surface 36 of the chuck 34 when the chuck 34 is placed on the sample container 28. This results in a stronger bond when the tissue sample and the embedding material are frozen to the chuck 34. If the embedding material is added to the sample container 28 before the tissue sample, then the embedding material may interfere with establishing optimal tissue "flatness".

In step 56, the sample container 28 is then placed on the freezing surface 24 of the freezing platform 22. If the sample container 28 and the tissue sample are transferred to the freezing surface 24 of the freezing platform 22 before the embedding material is added the tissue sample, then the tissue sample may freeze before a suitable bond is formed between the tissue sample and the embedding material. The sample container 28 is placed on the freezing platform 22 such that the bottom of the sample container 24 is flat on the freezing surface 24, rather than machining a cutout on the freezing platform and placing the sample container 24 within the cutout. This is because with the cutout, rapid cooling around the edges/flanges of the sample container 28 results which prevents the surface 36 of the chuck 34 from making a flat contact with the flanges 32 of the sample container 28. This in turn impairs the establishment of generally parallel planes between the surface 36 of the chuck 34 and the conforming plane of the bottom of the well 30 of the sample container 28.

Figure 6C:
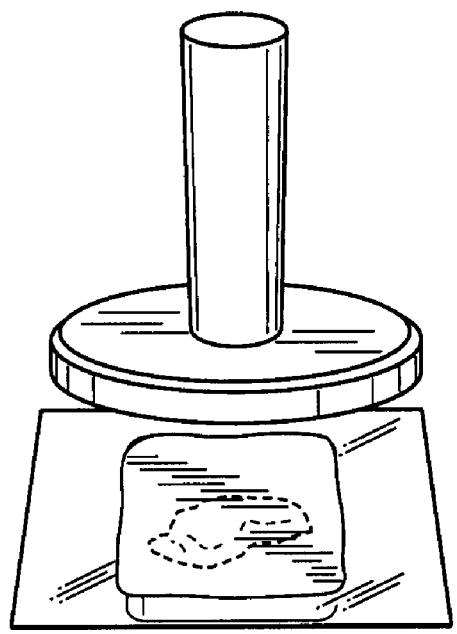
Figure 6D:
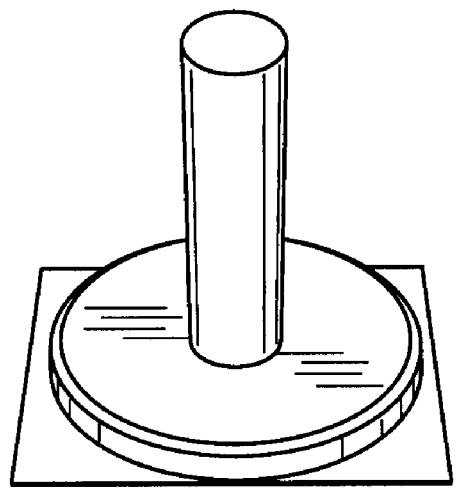

In step 58, the generally planar surface 36 of the chuck 34 is applied to the flanges of the sample container 28 before the embedding material and the sample tissue freeze thereby joining the tissue, embedding material, sample container and the chuck in a single step during freezing (see FIGS. 6C and 6D). This step renders the deep tissue margin generally parallel to the surface 36 of the chuck 34. This step is conducted for a first time period, which is on the order of several seconds.

Step 58 of the method 50 involves applying a room-temperature or near room-temperature chuck 34 to the sample container 28. The chuck 34 can be at a temperature in the range of 10 to 25 degrees Celsius. If a pre-cooled chuck is applied to the sample container 28, the embedding material freezes before the chuck 34 can properly sit flat on the flanges 32 of the sample container 28, which in turn impairs the ability to produce parallel planes for the generally planar surface 36 of the chuck 34 and the flanges 32 of the sample container 28 (and hence the frozen tissue specimen).

Once the tissue sample and embedding material have started to freeze, the true margin is anchored in place. The chuck 34 is then inverted and the chuck post 38 is placed into one of the holes 26 on the freezing platform 22 in step 60 for a second time period, of approximately 1-2 minutes, to accelerate the freezing process. The inverted chuck 34 allows for visual confirmation of the end point of freezing. As mentioned previously, there can also be some embodiments in which the chuck 34 does not have a post.

Once the freezing is complete, the sample container 28 can be removed from the chuck 34 and tissue specimen in step 62. This is done by peeling the sample container 28 from the chuck 34 and tissue specimen by gripping the bottom of the sample container 28, grabbing one edge/flange of the sample container 28 and then pulling. The frozen tissue specimen is then ready for sectioning. Due to the flat tissue samples that can be obtained with the method 50 and freezing apparatus, the sectioning plane of the microtome can be set approximately parallel to the full face, deep margin of the frozen tissue sample. With these planes aligned, true deep margin sections can be obtained with no block alignment required and minimal tissue loss due to trimming in. In accordance with standard techniques, the first full face section can be mounted on slides and stained with hematoxylin and eosin. The slides can then be examined for any signs of tumor.

In alternative embodiments, the freezing platform 22 may not have any holes 26. In these cases, once the chuck 34 is placed on the sample container 28, the chuck 34 and sample container 28 are left on the freezing platform 22 until the tissue sample and the embedding material have frozen.

The various embodiments of the freezing apparatus described herein are elegant, have a minimal design with a minimal number of components and require relatively low cost to manufacture and operate. The freezing apparatus and technique provide a consistent and accurate way for obtaining true, full-face deep margins from frozen sections for multiple tissue fragments, needle core biopsies, and irregular margins. Further, the use of a semi-transparent or transparent sample container with a flat base provides an ideal conforming plane to ensure complete flattening of the tissue sample prior to freezing. The sample container also provides a single-stage freezing technique (i.e. joining the chuck to the sample container), which used in conjunction with a room temperature, or near room temperature chuck, ensures that the conforming plane of the sample container is generally parallel to the generally planar surface of the chuck. Also, by processing in a freezing box, there is reduced clutter in the cryostat chamber, which results in a more organized workspace and a potentially reduced risk of technical error. In addition, the various embodiments of the apparatus and freezing technique can be applied to diagnostic tests having different frozen section requirements such as needle biopsies, for example, in which the tissue sample is a core sample that is difficult to process using conventional techniques.

It should be understood that various modifications can be made to the embodiments described and illustrated herein, without departing from the embodiments, the general scope of which is defined in the appended claims.

The invention claimed is:

1. An apparatus for preparing a frozen tissue specimen from an excised tissue sample, wherein the apparatus comprises:
   a) a freezing box including a first base, a lid that covers the first base, and a freezing chamber defined by the first base and the lid, the freezing chamber being sized and shaped to receive freezing agent, and the freezing box being made from a thermal insulating material for maintaining a reduced temperature environment in the freezing chamber for freezing the excised tissue sample;
   b) a freezing platform provided in the freezing box and including a flat freezing surface and at least one hole;
   c) at least one sample container, the sample container sized and shaped to receive the excised tissue sample and an embedding material, the at least one sample container including a well having a flat bottom that acts as a conforming plane for flattening the excised tissue thereon, walls and flat flanges connected at the upper portion of the walls to define a flat surface, the flat bottom made of a material that is at least semi-transparent to permit visual inspection of the excised tissue sample through the at least semi-transparent bottom of the sample container to confirm the tissue sample is sufficiently flattened before the embedding material is added and the tissue sample is frozen; and
   d) at least one chuck, the at least one chuck having a generally planar surface for placement on the flat flanges of the sample container and a post opposite the planar surface, the flat flanges and the chuck cooperating to ensure that the conforming plane of the sample container and the planar surface of the chuck remain parallel when the chuck is at or near room temperature and is placed on the sample container, and the embedding material is then frozen.

2. The apparatus of claim 1, wherein at least one of the flanges of the at least one sample container is longer than the other flanges of the at least one sample container.

3. The apparatus of claim 1, wherein at least one of the walls of the well of the at least one sample container is beveled.

4. The apparatus of claim 1, wherein the freezing agent comprises dry ice and the reduced temperature environment is at less than −70 degrees Celsius.

5. The apparatus of claim 4, wherein the freezing platform and the freezing chamber are sized to provide gaps between the freezing chamber and the freezing platform for receiving at least one of one or more pieces of dry ice and additional insulating material.

6. The apparatus of claim 1, wherein the freezing agent comprises one of compressed carbon dioxide gas, compressed liquid nitrogen, and a mechanical refrigeration compressor.

7. The apparatus of claim 1, wherein the thermal insulating material comprises polystyrene.

8. The apparatus of claim 1, wherein the freezing platform comprises anodized aluminum.

9. The apparatus of claim 1, wherein the freezing platform comprises one of copper, stainless steel, aluminum and alloys thereof.

10. The apparatus of claim 1, wherein the flat freezing surface comprises at least one of a bare metal, anodized, glazed, painted, and ceramic surface.

11. The apparatus of claim 1, wherein the holes extend from the top of the freezing platform to the bottom of the freezing platform.

12. The apparatus of claim 1, wherein the first base comprises shoulders for receiving and providing support for the freezing platform, the shoulders having a height for placing the upper surface of the freezing platform approximately level with the upper surface of the first base.

13. The apparatus of claim 1, wherein the first base comprises a first securing member and the lid comprises a complementary second securing member sized for releasably engaging the first securing member when the lid is placed on the first base.

14. The apparatus of claim 1, wherein the sample container is made from plastic material.

15. A method for preparing a frozen tissue specimen from an excised tissue sample, wherein the method comprises:
   a) placing the excised tissue sample into a sample container having a well with a lower flat bottom that acts as a conforming plane for the excised tissue sample, and upper flat flanges, the flat bottom made of a material that is at least semi-transparent, the sample container being at or near room temperature;
   b) flattening the excised tissue sample along the flat bottom of the well of the sample container;

c) visually inspecting the excised tissue sample through the at least semi-transparent bottom of the sample container to confirm that the tissue sample is sufficiently flattened;

d) after visually inspecting the tissue sample, then adding a sufficient amount of embedding material to the well of the sample container after the excised tissue sample has been flattened, wherein a top portion of the embedding material is above the flanges of the sample container;

e) placing the flat bottom of the sample container in a first orientation on a flat freezing surface of a freezing platform, the freezing platform being maintained at a reduced temperature for freezing the excised tissue sample and the embedding material;

f) placing a chuck being at or near room temperature on the sample container for a first time period, the chuck having a generally planar surface that is placed on the flat flanges of the sample container to maintain a flat contact surface therewith and ensure that the conforming plane of the sample container and the planar surface of the chuck are parallel to each other; and g) after freezing of the tissue sample and embedding material has started but before freezing is complete, inverting the chuck and placing the inverted chuck, tissue sample and sample container on the freezing platform in a second orientation for a second time period to complete freezing.

16. The method of claim 15, wherein the method further comprises:

once freezing of the tissue sample and embedding material is complete, removing the sample container from the chuck and tissue specimen after the excised tissue sample and the embedding material have frozen.

17. The method of claim 15, wherein the method further comprises maintaining the sample container and the chuck in the range of 10 to 25 degrees Celsius prior to freezing of the embedding material.

18. The method of claim 17, wherein the chuck comprises a post and the freezing platform comprises a hole sized to receive the post, and the inverting step further comprises placing the post into the hole.

19. The method of claim 17, wherein the method further comprises placing the freezing platform in a freezing chamber of a freezing box, and using a freezing agent in the freezing chamber for maintaining the freezing platform at a reduced temperature.

20. The method of claim 19, wherein the method further comprises using dry ice as the freezing agent to maintain the reduced temperature environment at less than −70 degrees Celsius.

21. The method of claim 19, wherein the method further comprises using one of compressed carbon dioxide gas, compressed liquid nitrogen, and a mechanical refrigeration compressor as the freezing agent.

22. The method of claim 15, further comprising manipulating the orientation of the tissue sample after visually inspecting the excised tissue sample through the at least semi-transparent bottom of the sample container and before adding embedding material to the well of the sample container.

23. The method of claim 15, wherein the step of visually inspecting the excised tissue sample through the at least semi-transparent bottom of the sample container includes inverting the sample container.

* * * * *